(12) United States Patent
Sano et al.

(10) Patent No.: US 8,895,296 B2
(45) Date of Patent: *Nov. 25, 2014

(54) ANALYZER

(75) Inventors: Minoru Sano, Hitachinaka (JP); Masato Ishizawa, Hitachinaka (JP); Shuhei Yamamoto, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/142,154

(22) PCT Filed: Dec. 10, 2009

(86) PCT No.: PCT/JP2009/070661
§ 371 (c)(1),
(2), (4) Date: Jun. 24, 2011

(87) PCT Pub. No.: WO2010/073917
PCT Pub. Date: Jul. 1, 2010

(65) Prior Publication Data
US 2011/0256532 A1 Oct. 20, 2011

(30) Foreign Application Priority Data
Dec. 25, 2008 (JP) ................. 2008-331057

(51) Int. Cl.
C12M 1/34 (2006.01)
C12M 3/00 (2006.01)
C12Q 1/68 (2006.01)
G01N 21/64 (2006.01)
G01N 21/66 (2006.01)

(52) U.S. Cl.
CPC .................... *G01N 21/645* (2013.01)
USPC .... 435/287.2; 435/6.1; 435/288.7; 422/82.08

(58) Field of Classification Search
CPC ... G01N 35/025; Y10S 435/808; B65B 43/60
USPC ................... 435/6.1, 287.2, 288.7; 422/82.08
See application file for complete search history.

(56) References Cited

U.S. PATENT DOCUMENTS 5,552,322 A * 9/1996 Nemoto et al. ............ 435/287.2
5,674,698 A * 10/1997 Zarling et al. .............. 435/7.92
(Continued)

FOREIGN PATENT DOCUMENTS

EP 1 895 307 A1 3/2008
JP 59-184844 10/1984
(Continued)

OTHER PUBLICATIONS

Fox, Trap Detectors and their Properties, 1991, Metrologia, 28, 197-202.*

(Continued)

*Primary Examiner* — Narayan Bhat
(74) *Attorney, Agent, or Firm* — McDermott Will & Emery LLP

(57) ABSTRACT

An object of the present invention relates to providing a nucleic acid analyzer capable of testing a plurality of test items in parallel, and of obtaining high efficiency of specimen processing even if the test item or a measuring object is changed. The present invention relates to an analyzer including a carousel rotatable about a rotation axis, a plurality of reaction containers held along a circumferential edge of the carousel, and at least one detector having a light source for irradiating the reaction container with excitation light and a detection element for detecting fluorescence from a reaction liquid in the reaction container. The detector is removable. By attaching a desired detector, it is possible to perform fluorescence measurement in response to the test item. According to the present invention, it is possible to test a plurality of test items in parallel, and even if the test item or the measuring object is changed, the high efficiency of specimen processing can be obtained.

16 Claims, 7 Drawing Sheets

(56) References Cited

U.S. PATENT DOCUMENTS

| | | | |
|---|---|---|---|
| 6,140,054 A * | 10/2000 | Wittwer et al. | 435/6.12 |
| 6,359,284 B1 | 3/2002 | Hayashi et al. | |
| 2005/0227274 A1 * | 10/2005 | Takahashi | 435/6 |
| 2006/0073584 A1 | 4/2006 | Sasaki et al. | |
| 2006/0141494 A1 | 6/2006 | Kambara et al. | |
| 2006/0223169 A1 * | 10/2006 | Bedingham et al. | 435/287.2 |
| 2006/0275892 A1 | 12/2006 | Shibazaki et al. | |

FOREIGN PATENT DOCUMENTS

| | | |
|---|---|---|
| JP | 4-106471 A | 4/1992 |
| JP | 06-160401 | 6/1994 |
| JP | 2000-088752 A | 3/2000 |
| JP | 2001-208760 A2 | 8/2001 |
| JP | 2002-116148 A2 | 4/2002 |
| JP | 2002-277389 A2 | 9/2002 |
| JP | 2005-052148 A | 3/2005 |
| JP | 2006-122041 A | 5/2006 |
| JP | 2006-177837 A | 7/2006 |
| JP | 2007-185101 | 7/2007 |
| JP | 2007-271361 A2 | 10/2007 |
| JP | 2008-058123 A2 | 3/2008 |
| JP | 2008-534966 A | 8/2008 |
| WO | 2005/054844 A1 | 6/2005 |
| WO | 2006/107627 A1 | 10/2006 |
| WO | WO 2008/114372 A1 | 9/2008 |

OTHER PUBLICATIONS

Japanese Office Action, issued in Japanese Patent Application No. 2008-331057, dated May 15, 2012.

Japanese Office Action issued in Japanese Patent Application No. 2008-331057 dated Sep. 11, 2012.

Japanese Office Action with English translation issued in Japanese Application No. 2013-079955 issued Feb. 4, 2014.

Japanese Office Action issued in Japanese Patent Application No. 2008-331057 dated Feb. 5, 2013.

* cited by examiner

ANALYZER

RELATED APPLICATIONS

This application is the U.S. National Phase under 35 U.S.C. §371 of International Application No. PCT/JP2009/070661, filed on Dec. 10, 2009, which in turn claims the benefit of Japanese Application No. 2008-331057, filed on Dec. 25, 2008, the disclosures of which Applications are incorporated by reference herein.

TECHNICAL FIELD

The present invention relates to an analyzer for analyzing a biologically-related substance, and for example, relates to an analyzer for analyzing nucleic acid.

BACKGROUND ART

As a nucleic acid amplification method, for example, the PCR method is known. In the PCR method, nucleic acid contained in a specimen is amplified in a base sequence-specific manner to detect a trace of nucleic acid with high sensitivity. Generally in the nucleic acid amplification method, a fluorophore is used for nucleic acid labeling, and changes in fluorescence intensity are chronologically tracked to perform an analysis. Additionally, in an amplification process, temperatures of a reaction liquid are controlled to facilitate a reaction.

JP Patent Publication (Kokai) No. 2002-116148 A (Patent Document 1) discloses a fluorescence-type plate analyzing device in which reaction containers, each of which is referred to as a "well", are arranged in lattice form on a quadrate plate. In this device, irradiation and detection optical systems are provided on a bottom side of the plate. The plate is moved along a horizontal plane in longitudinal and lateral directions, to detect fluorescence from a sample held in the well. Additionally, in this device, the fluorescence is detected not only at a single detection position but also at a plurality of detection positions to perform fluorescence measurement efficiently. Moreover, LEDs (Light-Emitting Diodes) are used as the excitation light source for the purpose of providing a low-price and compact-size device in which it is easy to maintain an excitation light source.

Patent Document 1: JP Patent Publication (Kokai) No. 2002-116148 A

DISCLOSURE OF THE INVENTION

Problems to be Solved by the Invention

The inventors of the present application have conducted concentrated studies on a nucleic acid analyzer suitable for a clinical test, and found knowledge as described below.

In the clinical test, there is a need to obtain test results with respect to a plurality of test items from a specimen. In addition, for the purpose of improving efficiency of testing items, it would be efficient if a plurality of test items could be processed in parallel. It is desirable to assign a different fluorophore to each of measuring objects, as a marker of nucleic acid amplification. Besides, it is desirable to measure two types of fluorophores of a measuring object and an internal standard respectively in parallel, in addition to setting a plurality of test items. Further, in a clinical test, the test items or the measuring objects are frequently changed, increased, or decreased, and therefore it is required to be able to respond to an emergent measurement or test.

An object of the present invention is to provide a nucleic acid analyzer capable of testing a plurality of test items in parallel, and of obtaining high efficiency of specimen processing even if a test item or a measuring object is changed.

Means for Solving the Problems

The present invention relates to an analyzer comprising a carousel rotatable about a rotation axis, a plurality of reaction containers held along a circumferential edge of the carousel, and at least one detector including a light source for irradiating the reaction container with excitation light and a detection element for detecting fluorescence from a reaction liquid in the reaction container. The detector is removable. By attaching a desired detector, it is possible to perform fluorescence measurement in response to a test item.

Effects of the Invention

According to the present invention, it is possible to test a plurality of test items in parallel, and even if the test item or a measuring object is changed, high efficiency of specimen processing can be obtained.

DESCRIPTION OF SYMBOLS

Figure 1A:
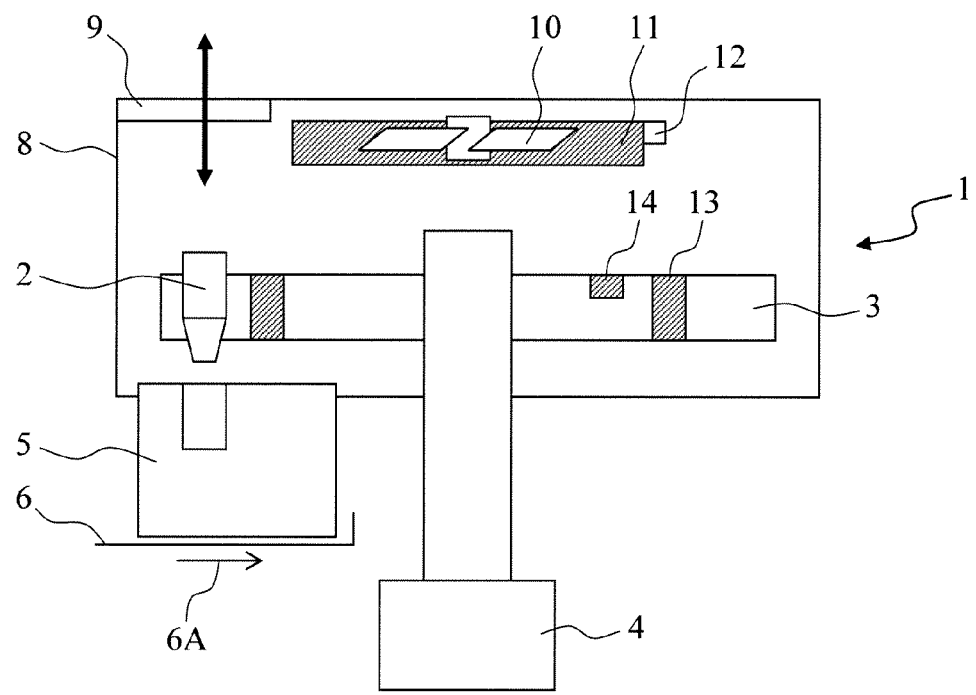
FIG. 1A is an explanatory view showing a first example of a cross-sectional structure of a main part of an analyzer.

1 Reading unit
2 Reaction container
3 Carousel
4 Driving mechanism
5 Detector
6 Slot
8 Casing
9 Gate
10 Fan
11 Heat source
12 Temperature sensor
13 Heat source
14 Temperature sensor 15 Douser
16 Shutter
21 Light source
22 Condenser
23 Excitation filter
24 Fluorescence filter
25 Photodiode
26 Dichroic mirror

BEST MODE FOR CARRYING OUT THE INVENTION

An embodiment discloses a nucleic acid analyzer comprising a carousel rotatable about a rotation axis, a plurality of reaction containers held along a circumferential edge of the carousel, and at least one detector including a light source for irradiating the reaction container with excitation light and a detection element for detecting fluorescence from a reaction liquid in the reaction container, wherein the detector is removably attached, and the detectors are configured to perform fluorescence measurement independently of one another.

Also, an embodiment discloses a nucleic acid analyzer wherein each of a plurality of detectors is configured to comprise a light source for generating excitation light having a wavelength different from one another and a detection element for detecting fluorescence having a wavelength different from one another.

Additionally, an embodiment discloses a nucleic acid analyzer wherein each of a plurality of detectors is selected such that the difference between wavelengths of excitation lights generated by light sources of the adjacent two detectors is larger than a predetermined wavelength difference, and the difference between wavelengths of fluorescences detected by detection elements of the adjacent two detectors is larger than a predetermined wavelength difference.

Moreover, an embodiment discloses a nucleic acid analyzer wherein each of a plurality of detectors is configured to comprise a light source for generating excitation light having the identical wavelength and a detection element for detecting fluorescence having the identical wavelength.

Besides, an embodiment discloses a nucleic acid analyzer wherein amplification gains with respect to output signals from a plurality of detectors are set to be different from one another.

Also, an embodiment discloses a nucleic acid analyzer wherein resolutions of output signals from a plurality of detectors are set to be different from one another.

Additionally, an embodiment discloses a nucleic acid analyzer wherein a douser is provided between adjacent two detectors of a plurality of detectors.

Moreover, an embodiment discloses a nucleic acid analyzer configured such that a detector is provided with an openable and closable shutter; and when the detector optically detects a reaction solution in a reaction container, the shutter opens; and when the detector does not optically detect the reaction solution in the reaction container, the shutter closes.

Besides, an embodiment discloses a nucleic acid analyzer wherein a light source of a detecting device comprises a light-emitting diode, and a detection element comprises a photodiode.

Also, an embodiment discloses a nucleic acid analyzer comprising a slot for removably supporting a detector; and configured such that the detector can be removed or attached by moving the detector along the slot.

Additionally, an embodiment discloses a nucleic acid analyzer wherein there is provided a temperature controlling device for keeping temperatures of a reaction container and a reaction liquid in the reaction container at predetermined temperatures.

Moreover, an embodiment discloses a nucleic acid analyzer wherein a temperature controlling device comprises a fan, a heat source, and a temperature sensor.

Besides, an embodiment discloses a nucleic acid analyzer wherein a temperature controlling device comprises a heat source and a temperature sensor which are provided in a carousel.

Also, an embodiment discloses a nucleic acid analyzer wherein there is provided a casing for accommodating at least a carousel and a reaction container; the casing comprises an openable and closable gate; and the reaction container can be taken in and out via the gate.

Additionally, an embodiment discloses a nucleic acid analyzer comprising a carousel rotatable about a rotation axis, a plurality of reaction containers held along a circumferential edge of the carousel, at least one detector including a light source for irradiating the reaction container with excitation light and a detection element for detecting fluorescence from a reaction liquid in the reaction container, and a temperature controlling device for keeping temperatures of a reaction container and a reaction liquid in the reaction container at predetermined temperatures, wherein the detector is removably attached, and the detectors are configured to perform fluorescence measurement independently of one another.

Moreover, an embodiment discloses a nucleic acid analyzer configured such that a carousel is operated based on a cycle consisting of a container setting period for stopping the carousel in order to place or remove a reaction container and a fluorescence measurement period for rotating the carousel at a constant speed; and in the fluorescence measurement period, the detector measures fluorescence intensity when the reaction container is passing a detection position on a detector.

Besides, an embodiment discloses a nucleic acid analyzing method for analyzing nucleic acid using a carousel rotatable about a rotation axis, wherein a plurality of reaction containers are placed along a circumferential edge of the carousel; a plurality of detectors placed along an outer circumference of the carousel measure fluorescence from a reaction solution contained in the reaction container while rotating the carousel, each of the plurality of detectors performing fluorescence measurement of a predetermined reaction solution independently of one another; and when the number or type of reaction containers is to be changed, the detector is added or removed.

Also, an embodiment discloses a nucleic acid analyzing method wherein a plurality of detectors detect fluorescence having wavelengths different from one another.

Hereinafter, above-mentioned and other novel features and effects of the present invention will be described with reference to the drawings. It is to be noted that the drawings are used exclusively for the understanding of the present invention, and by no means limit the scope of right.

Embodiments

Figure 1B:
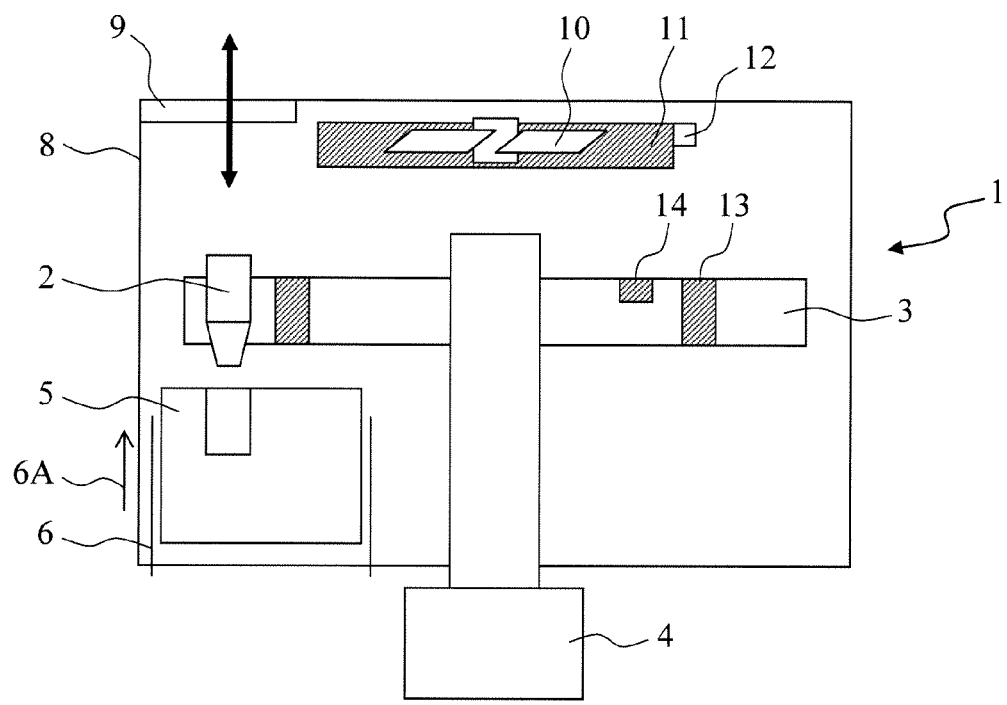
FIG. 1B is an explanatory view showing a second example of a cross-sectional structure of a main part of an analyzer.
Figure 2:
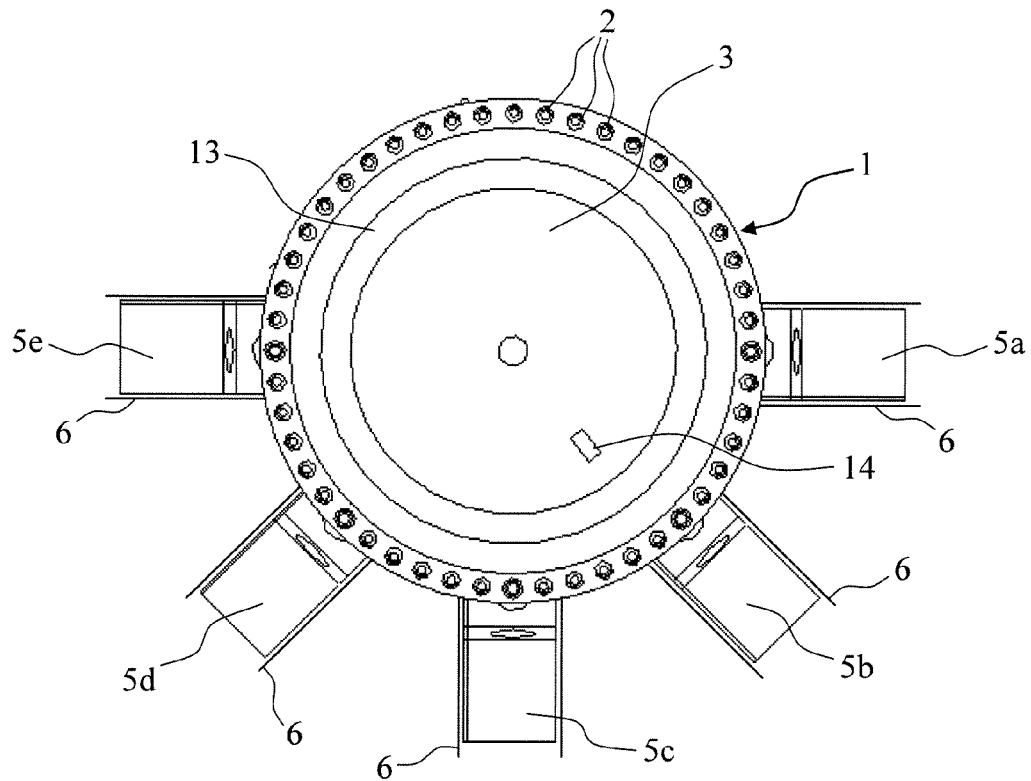
FIG. 2 is an explanatory view showing an example of a planar structure of a main part of an analyzer.

With reference to FIG. 1A, FIG. 1B, and FIG. 2, an example of a reading unit, which is a main part of an analyzer, will be described. A reading unit 1 of the present example includes a plurality of reaction containers 2 for accommodating reaction liquids which are targets for analysis, a carousel 3 for holding the reaction containers 2, a driving mechanism 4 for rotating the carousel, at least one detector 5 arranged along a circumference of the carousel 3, and a casing 8.

The carousel 3 includes a circular plate-shaped disk made of aluminum alloy, and is rotatable about a central axis. On an edge of the carousel 3, the numerous reaction containers 2 are held. The detectors 5 are arranged along the circumference of the carousel 3 at regular intervals. The detectors 5 are arranged beneath the reaction container 2. In the example of FIG. 1A, the detectors 5 are provided outside of the casing 8. However, in the example of FIG. 1B, the detectors 5 are provided inside of the casing 8. Here, five detectors 5 are provided. However, any number of detectors 5 other than five may be provided.

The detector 5 is exchangeable, and is freely attached and removed. The detector 5 is inserted into a slot 6. The slot 6 may be configured so as to extend along a radial direction as the example shown in FIG. 1A. However, the slot 6 may be configured so as to extend along an axial direction as the example shown in FIG. 1B. Further, although not illustrated, the slot 6 may be arranged to be inclined with respect to the axial direction. That is, the slot 6 may be arranged along a conical surface. The detector 5 may be mounted by moving the detector 5 inwardly along the slot 6 as shown by an arrow 6A. The detector 5 may be removed by moving the detector 5 outwardly along the slot 6 in a direction opposite to the direction of the arrow 6A. In the slot 6, a snap-type fastening device may be provided. As shown by the arrow 6A, when the detector 5 is moved along the slot 6 inwardly, the detector 5 engages with the fastening device at a predetermined position, and cannot be moved any more. When the detector 5 is to be removed, the fastening device is released. The detector 5 may be fixed by a screw in place of the fastening device.

According to the present example, the detectors 5 can detect or measure the reaction liquids in the reaction containers 2 independently of one another. Accordingly, in the case where one of detectors goes out of order or maintenance of a detector is required, it is required to remove only the detector. In this case, the remaining detectors can be used without change. That is, no special tasks with respect to the remaining detectors are required. Removal of the detector does not affect detection sensitivity in the remaining detectors. Accordingly, it is possible to make test results coincident with each other before and after the tasks.

As shown in FIG. 1A and FIG. 1B, the casing 8 of the present example is provided with an openable and closable gate 9. It is to be noted that in FIG. 2, the casing 8 has been removed. At least, the reaction container 2 and the carousel 3 are accommodated in the casing 8. By the casing 8 being provided in this way, it is possible to keep a temperature in the casing 8 constant. Further, by the casing 8 being provided, it is possible to prevent irradiation of unnecessary light to the reaction container 2, and furthermore, to prevent incidence of unnecessary light into the detector 5. When the reaction container 2 is mounted to the carousel 3, the mounting is performed via the gate 9. Accordingly, when the reaction container 2 is mounted, it is not required to remove a whole of the casing 8.

The reading unit 1 of the present example further includes a temperature controlling device for keeping the temperature of the reaction liquid accommodated in the reaction container 2 at a predetermined temperature. The temperature controlling device of the present example includes a fan 10, a heat source 11, and a temperature sensor 12. The fan 10, the heat source 11, and the temperature sensor 12 are provided near a ceiling of the casing 8. Similarly, the carousel 3 may also be provided with the heat source 13 and the temperature sensor 14.

Since air in the casing 8 is circulated by the fan 10, air stagnation in a specific area in the casing 8 is prevented. In particular, air around the reaction container is circulated, and therefore air stagnation around the reaction container is prevented. As the temperature sensors 12 and 14, normal sensors may be used, each of which is configured so as to bring a thermosensor into contact with an object to be measured; however, a noncontact infrared thermometers may be used. The infrared thermometer enables noncontact temperature measurement of the reaction container and the reaction liquid. Here, explanations have been made as to a first temperature controlling device provided near the ceiling of the casing 8 and a second temperature controlling device provided in the carousel 3. According to the present invention, either of the first temperature controlling device or the second temperature controlling device may be provided, however, both of such devices may be provided.

The analyzer of the present example is applicable to analyzers for various specimens. However, here, an explanation will be made citing the nucleic acid analyzer as an example. Additionally, as an example of the reading unit, a case where the fluorescence is detected will be described. The detector 5 includes an excitation light source for irradiating the reaction container 2 held by the carousel 3 with excitation light. As this excitation light source, the light-emitting diode (LED), a gas laser, a semiconductor laser, a xenon lamp, a halogen lamp, or the like may be used. However, as the excitation light source, the light-emitting diode is preferably used.

A sample solution containing fluorescence-labeled nucleic acid and the like is held in the reaction container. When the reaction container 2 is irradiated with the excitation light from the excitation light source, the reaction liquid generates the fluorescence. The detector includes a detection element for detecting the fluorescence from the reaction liquid. As this detection element, a photodiode, a photomultiplier, CCD, or the like is used. However, as the detection element, the photodiode is preferably used.

Temperature control for facilitating nucleic acid amplification includes periodic control for changing temperatures cyclically and stepwisely as in the case of the PCR method, and constant-temperature control for keeping a predetermined temperature for a predetermined period of time as in the case of the NASBA method or the LAMP method. Further, in the case where the nucleic acid analyzer is under a comparatively high-temperature environment, an air conditioner is required. Thus, as the heat sources 11 and 13, preferred are not only warming elements like heaters but also temperature controlling elements with cooling functions such as Peltier elements.

An explanation will be made as to a case where the nucleic acid is amplified using the analyzer of the present example by means of a nucleic acid amplification method. In the nucleic acid amplification method, by taking fluorescent substances into synthetic products quantitatively, it is possible to chronologically monitor the synthetic products. Here, an explanation will be made as to a case where the NASBA method, which is one of the nucleic acid amplification methods, is performed. The NASBA method is one of constant-temperature amplification methods capable of amplification by use of only one temperature. In the present example, this temperature is 41 degrees. It is known that in the light-emitting diode (LED) used as the excitation light source, due to a change in temperature of the LED itself, a peak wavelength and an amount of light are changed. Thus, both of the first temperature controlling device provided near the ceiling of the casing 8 and the second temperature controlling device provided in the carousel 3 are used, and therefore it is possible to keep the temperature around the light-emitting diode (LED) at 41 degrees. This makes it possible to eliminate unevenness of light-emitting characteristics of the light-emitting diode (LED) and to hold the temperature of the reaction container 2 at 41 degrees.

The reaction container 2 accommodates the reaction liquid containing a specimen and a base labeled by the fluorescent substance. The reaction containers 2 are sequentially loaded into the carousel in a predetermined cycle, and the fluorescence measurement is performed.

An operational cycle of the carousel consists of the container setting period and the fluorescence measurement period. In the container setting period, the carousel is stopped, and the reaction container is placed or removed. In the fluorescence measurement period, the fluorescence measurement is performed while rotating the carousel at a constant speed. In the fluorescence measurement period, the fluorescence intensity is measured when the reaction container is passing a detection position on the detector. The lengths of the container setting period and the length of the fluorescence measurement period are constant, and the setting and the measurement are repeated in a predetermined cycle.

Every time the carousel makes one rotation, the reaction container passes all of the detectors circumferentially placed. To each of the detectors, the fluorescence of the wavelength to be measured has been assigned. Each of the detectors independently detects the fluorescence having the wavelength assigned thereto. In each of the reaction containers 2, the identical specimen has been collected. Data measured by each of the detectors is accumulated as a chronological change of the reaction liquid in an external computer, and further, is externally output as a quantitative analytical result.

According to the present example, if a test item is newly developed, or a new fluorophore is adopted, the detector 5 is added or exchanged. Accordingly, even if the test items are increased, or the types of the fluorophore are changed, it is not required to introduce a new nucleic acid analyzer.

As mentioned above, normally, fluorescence measurements of the wavelengths different from one another are assigned to the detectors respectively. That is, the detectors each detect the fluorescences of the wavelengths being different from one another respectively. However, the identical wavelength may be assigned to the plurality of detectors. Here, an explanation will be made as to a case where the plurality of detectors measure the fluorescence having the identical wavelength.

First, an explanation will be made as to a method in which a measurement range is optimized by giving a different gain to each detector. For example, the fluorescence having the identical wavelength is assigned to a first detector 5a and a second detector 5b. However, a configuration is made such that the gain of signal amplification in the first detector 5a is different from that in the second detector 5b. That is, the amplification gains different from one another are given. This makes it possible to optimize a range of the fluorescence intensity able to be measured. For example, the gain of the first detector 5a is set to be low, whereas the gain of the second detector 5b is set to be high. In the case where the concentration of the specimen to which the nucleic acid amplification is performed is high, the fluorescence is detected by the first detector 5a. The first detector 5a has a low gain and therefore a high detection limit. Accordingly, even if the specimen has a high concentration, the fluorescence can be detected. In the case where the concentration of the specimen is low, the fluorescence is detected by the second detector 5b. The second detector 5b has a high gain and therefore a low detection limit. Accordingly, even if the specimen has a low concentration, the fluorescence can be detected. Two detectors detect the fluorescence having the identical wavelength. However, the two detectors have the different gains, and therefore, it is avoided that the fluorescence cannot be detected because the fluorescence is beyond the detection limit. That is, the measurement range can be optimized by changing the gain for each detector. This makes it possible to lower a risk of wasting the specimen.

In order to give a different gain for each detector, a different gain may be given to each signal amplifier which is placed after the output signal from detector is converted into a voltage signal. However, even if a different detection element such as a photodiode or a photomultiplier is incorporated in each of the detectors, the similar result can be obtained.

Next, an explanation will be made as to a method in which the resolution is optimized by giving a different bit resolution to each detector. For example, an A/D convertor of the first detector 5a has the resolution of 8 bits, whereas the A/D convertor of the second detector 5b has the resolution of 16 bits. The 8 bits is a low resolution on the assumption that the specimen has the normal concentration. The 16 bits is a high resolution on the assumption that the specimen has a low concentration. Since in this way, the fluorescence of the specimen having a normal concentration is assigned to the first detector 5a and the fluorescence of the specimen having a low concentration is assigned to the second detector 5b, it is possible to detect a minute difference in concentration.

As a method for giving a different bit resolution to each detector, a different bit resolution may be given to the A/D convertor for each detector. However, the number of integration of the obtained data may be changed for each detector.

Further, to a plurality of detectors, the identical wavelengths may be assigned, and the identical amplification gains may be given. In this case, the identical detection result can be obtained from a plurality of detectors. However, resistance to a failure or a device error increases. In the present example, in the reaction containers placed in the carousel 3, the identical specimens have been collected. Accordingly, if the reaction container or the detector is changed, only the effect due to this change can be reflected on an analytical result, resulting in an improvement in reliability of measurement data.

Here, the explanation has been made citing the nucleic acid analyzer as the example. However, the present invention is by no means limited to the nucleic acid analyzer, and is applicable to devices for analyzing the specimens collected from biological bodies at large. In addition, the explanation has been made as to the case where fluorescence detection is performed as the example of the reading unit. However, the present invention is applicable also to the case where the target for analysis is detected by means of methods other than the fluorescence detection.

Figure 3:
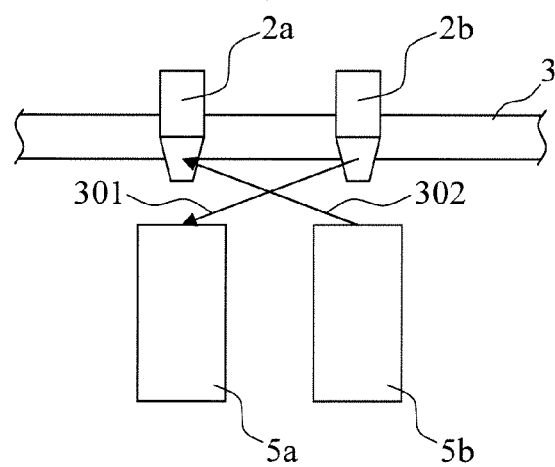
FIG. 3 is an explanatory view showing a mechanism in which crosstalk occurs between adjacent detectors in an analyzer.

With reference to FIG. 3, an explanation will be made as to crosstalk. In the case where a plurality of fluorophores are detected, mixture of the fluorescence between adjacent detectors is highlighted as a problem. This crosstalk causes the S/N ratio to be lowered in the nucleic acid analyzer which performs the fluorescence measurement. It is assumed that when the first detector 5a detects the fluorescence from the first reaction container 2a, the second detector 5b simultaneously detects the fluorescence from the second reaction container 2b.

The crosstalk detected by the first detector 5a will be considered. If the first detector 5a detects fluorescence 301 from the adjacent second reaction container 2b, it causes the crosstalk. If the first reaction container 2a is irradiated with the excitation light 302 from the adjacent second detector 5b, it generates the fluorescence. If this fluorescence is detected by the first detector 5a, it causes the crosstalk.

Figure 4A:
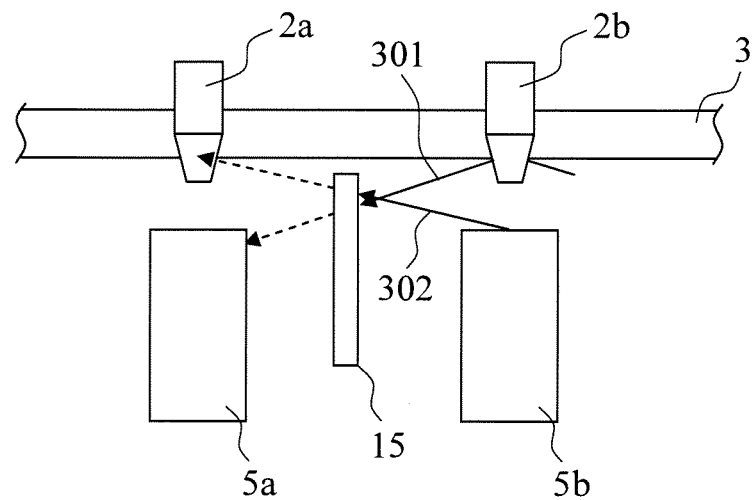
FIG. 4A is an explanatory view showing a means for preventing crosstalk between adjacent detectors in a main part of an analyzer.
Figure 4B:
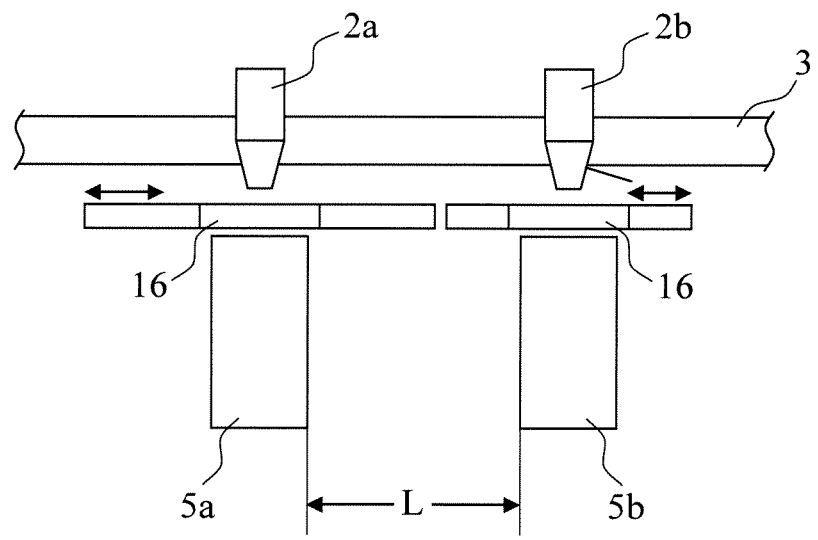
FIG. 4B is an explanatory view showing a means for preventing crosstalk between adjacent detectors in a main part of an analyzer.

With reference to FIG. 4A and FIG. 4B, an explanation will be made as to a means for preventing the crosstalk by means of the present invention. In an example shown in FIG. 4A, a douser 15 is provided between the first detector 5a and the second detector 5b. The douser 15 prevents the fluorescence 301 from the adjacent second reaction container 2b from reaching the first detector 5a, and further, prevents the first reaction container 2a from being irradiated with the excitation light 302 from the adjacent second detector 5b. In an example shown in FIG. 4B, each of the detectors 5a and 5b is provided with a shutter 16. The shutter 16 is configured so as to block an excitation-light irradiation port or a fluorescence reading port of the detector. The shutter 16 provides a function similar to the function of the douser 15.

The shutter 16 may be configured so as to be closed when the reaction container, the fluorescence of which is not to be measured, is located at the detection position, and be opened when the reaction container, the fluorescence of which is to be measured, is located at the detection position. Further, as shown in FIG. 4B, a distance L between adjacent two detecting devices may be made sufficiently large. This makes it possible to obtain the function similar to that of the douser 15 or the shutter 16. That is, the fluorescence 301 from the adjacent second reaction container 2b is prevented from reaching the first detector 5a. Further, the first reaction container 2a is prevented from being irradiated with the excitation light 302 from the adjacent second detector 5b. It is to be noted that an interval between the adjacent reaction containers 2a and 2b may be made large. However, if the interval L between the reaction containers 2a and 2b is too large, the number of reaction containers to be placed in the carousel decreases. Accordingly, the interval L between the reaction containers 2a and 2b is in a predetermined range.

Here, as the means for preventing the crosstalk, the douser 15, the shutter 16, and the case where the distance L between the two detecting devices is made large have been explained. Some of these three means may be appropriately combined.

Figure 5A:
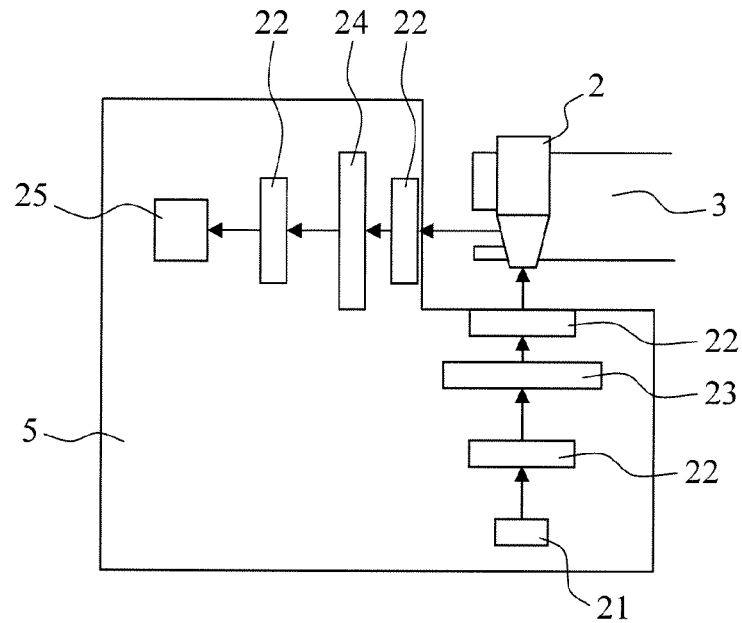
FIG. 5A is an explanatory view showing an example of an optical system of a detector of an analyzer.

With reference to FIG. 5A, an explanation will be made as to a first example of an optical system of the detector 5. The optical system includes an excitation optical system and a detection optical system. The excitation optical system includes a light source 21, condensers 22, and an excitation filter 23. The detection optical system includes the condensers 22, a fluorescence filter 24, and a photodiode 25. In the present example, the bottom surface of the reaction container 2 is irradiated with the excitation light, and the fluorescence is detected from a reading port opened on a side of the reaction container 2. It is to be noted that in the example of FIG. 5A, the shutter 16 which is shown in FIG. 4B is not illustrated, however, the shutter 16 may be provided.

Figure 5B:
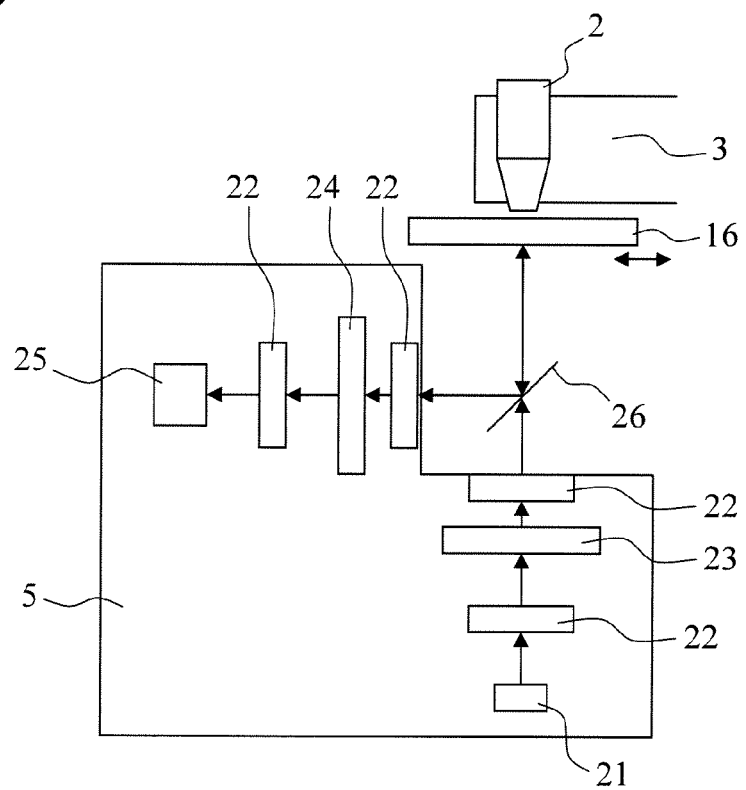
FIG. 5B is an explanatory view showing an example of an optical system of a detector of an analyzer.

With reference to FIG. 5B, an explanation will be made as to a second example of the optical system of the detector 5. The optical system includes the excitation optical system, the detection optical system, a dichroic mirror 26, and the shutter 16. The excitation optical system includes the light source 21, the condensers 22, and the excitation filter 23. The detection optical system includes the condensers 22, the fluorescence filter 24, and the photodiode 25.

Figure 6:
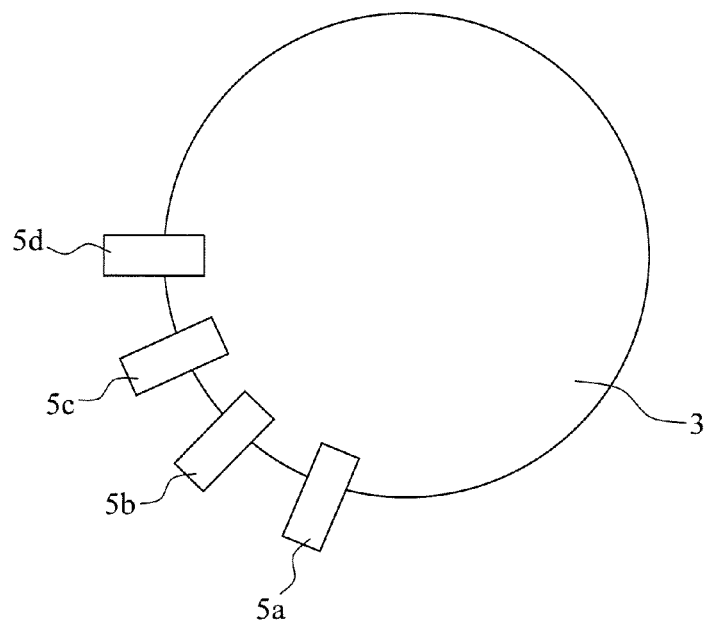
FIG. 6 is an explanatory view showing an example of an array structure of a detector of an analyzer.
Figure 7:
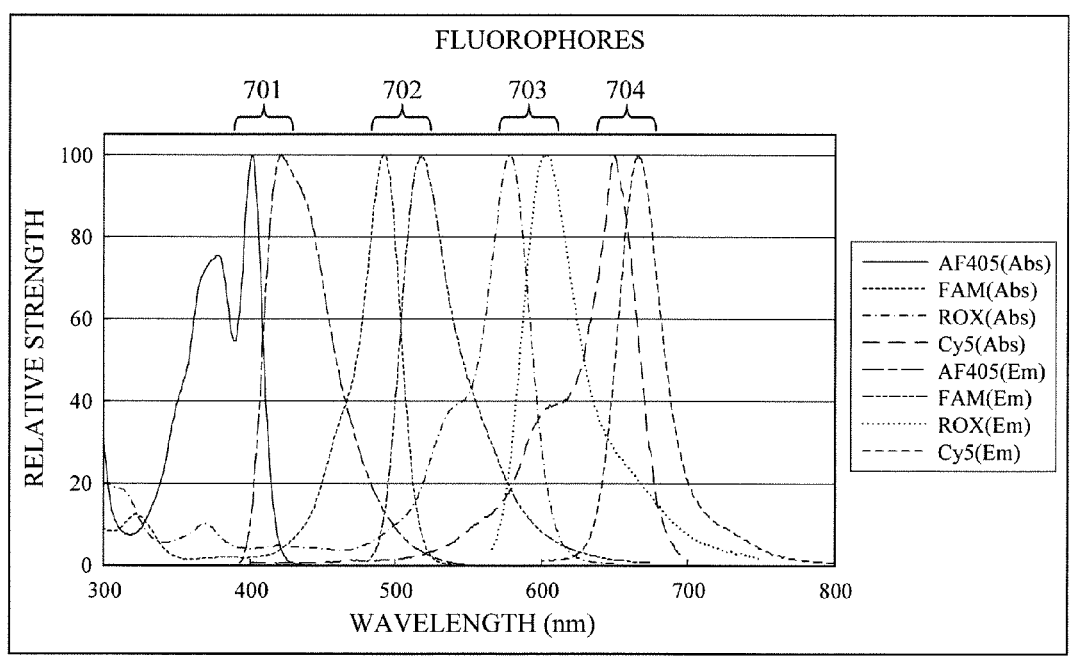
FIG. 7 is an explanatory view showing an example of peak wavelengths of fluorophores.

With reference to FIG. 6 and FIG. 7, an explanation will be made as to another example of the means for preventing the crosstalk. As shown in FIG. 6, four detectors 5a, 5b, 5c, and 5d are sequentially arranged in parallel along the circumference of the carousel 3. According to the present example, these detectors are selected such that a difference in wavelengths of the excitation light generated by the light sources of the two detectors adjacent with each other is larger than a predetermined difference in wavelengths. Further, these detectors are selected such that a difference in wavelengths of the fluorescence detected by the detection elements of the two detectors adjacent with each other is larger than a predetermined difference in wavelengths. Here, detected is the fluorescence from four fluorophores of FAM, ROX, Cy5, and Alexa405. FIG. 7 shows the wavelength of the excitation light and the wavelength of the fluorescence of the respective four fluorophores of FAM, ROX, Cy5, and Alexa405. Two peaks 701 near the wavelength 400 nm represent an absorption wavelength and a radiation wavelength of the fluorophore Alexa405. Two peaks 702 near the wavelength of 500 nm represent the absorption wavelength and the radiation wavelength of the fluorophore FAM. Two peaks 703 near the wavelength of 600 nm represent the absorption wavelength and the radiation wavelength of the fluorophore ROX. Two peaks 704 near the wavelength of 650 to 700 nm represent the absorption wavelength and the radiation wavelength of the fluorophore Cy5. Especially between the two fluorophores of FAM and ROX, and between the two fluorophores of ROX and Cy5, the crosstalks are large. Thus, the detectors of the two fluorophores are arranged so as not to be adjacent with each other. For example, the fluorophore ROX may be assigned to the first detector 5a; the fluorophore Alexa405 to the second detector 5b; the fluorophore Cy5 to the third detector 5c; and the fluorophore FAM to the forth detector 5d. The assignments other than the above-mentioned assignments may be made, if the detectors with respect to the two fluorophores of FAM and ROX are not adjacent, and the detectors with respect to the two fluorophores of ROX and Cy5 are not adjacent.

Figure 8:
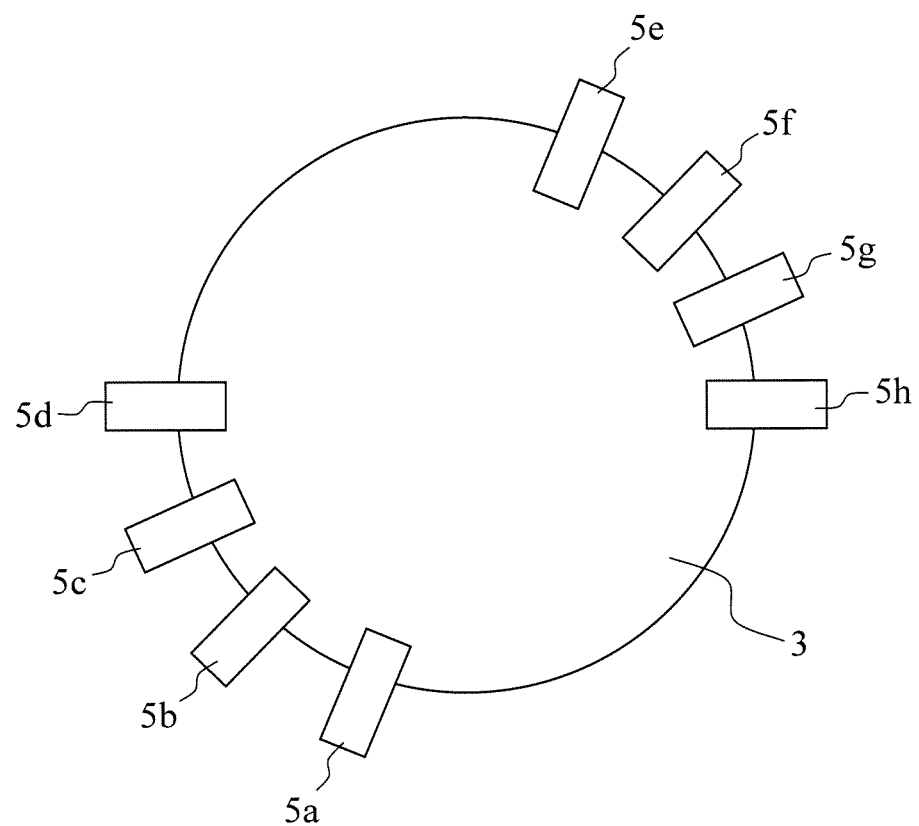
FIG. 8 is an explanatory view showing another example of an array structure of a detector of an analyzer.

With reference to FIG. 8, an explanation will be made as to an example of a means for improving reliability of the analytical result. Reagents, consumable items, and the like for the nucleic acid amplification used in the nucleic acid analyzer generally have higher prices and higher contamination risks, compared with those in a biochemical or immune device. Thus, required is the higher reliability with respect to the analytical result.

In the present example, as shown in FIG. 8, eight detectors 5a, 5b, 5c, 5d, 5e, 5f, 5g, and 5h are sequentially arranged in parallel along the circumference of the carousel 3. In the present example, the detectors 5a, 5b, 5c, and 5d of a first group have the configurations identical to those of the detectors 5e, 5f, 5g, and 5h of a second group. That is, each of pairs of the detectors arranged at both ends of a diameter of the carousel 3 has the identical configuration. For example, the first detector 5a and the fifth detector 5e have the identical configuration, which generates the excitation light having the identical wavelength and detects the fluorescence having the identical wavelength. Similarly, the second detector 5b and the sixth detector 5f have the identical configuration, which generates the excitation light having the identical wavelength and detects the fluorescence having the identical wavelength. The third detector 5c and the seventh detector 5g have the identical configuration, which generates the excitation light having the identical wavelength and detects the fluorescence having the identical wavelength. The forth detector 5d and the eighth detector 5h have the identical configuration, which generates the excitation light having the identical wavelength and detects the fluorescence having the identical wavelength. When the carousel 3 makes one rotation, two of the measurement data by means of the pair of detectors are obtained for each of the fluorophores of the reaction liquid in each of the reaction containers. The measurement data obtained by the pair of detectors should be identical. For example, the identical measurement results should be obtained by the first detector 5a and the fifth detector 5e. If the identical measurement results are not obtained, it is determined that the detectors are under abnormal conditions, or it is determined that processing such as data processing or display processing is under abnormal conditions. If the cause of the abnormal conditions is found out and it is found that one of the pair of detectors is out of order, it is possible to determine that the other of detectors is under normal conditions. In this case, the measurement data from the detector which is determined to be under normal conditions is adopted, and therefore it is possible to eliminate a need for performing the measurement again. Thus, it is possible to output the analytical results without wasting the valuable specimen.

In the present example, the data at two points with respect to the identical sample can be obtained. Thus, by creating an approximation curve from a lot of data points, it is possible to improve precision of the approximation curve. Therefore, the analytical results having high precision can be obtained.

Further, in the pair of detectors corresponding to each other between the first group of the detectors $5a$, $5b$, $5c$, and $5d$, and the second group of the detectors $5e$, $5f$, $5g$, and $5h$, it is assumed that one of constituent elements and measurement parameters is set to be different, and the other constituent elements and measurement parameters are made identical. If this leads to different results, it is possible to determine that such results are attributed to the different constituent element or measurement parameter.

In this way, it is possible to determine which of the constituent elements and the measurement parameters affects the measurement results, and which of them does not affect them. Further, with respect to the constituent element or the measurement parameter which affects the measurement results, it is possible to know how they affect such results.

As described above, the explanations have been made to the examples of the present invention. However, it will be readily understood by a person skilled in the art that the present invention is by no means limited to the above-mentioned examples, and various modifications may be made thereto in the scope of the invention recited in the appended claims.

The invention claimed is:

1. A nucleic acid analyzer comprising:
a carousel rotatable about a rotation axis,
a plurality of reaction containers held along a circumferential edge of the carousel, and
a plurality of detectors each including a light source for irradiating the reaction container with excitation light and a detection element for detecting fluorescence from a reaction liquid in the reaction container, wherein:
the detectors are arranged along the circumference of the carousel, and each of the plurality of detectors are configured to perform fluorescence measurement independently of one another,
the carousel is configured for operation based on a cycle comprising:
a container setting period for stopping the carousel in order to place or remove the reaction container, and
a fluorescence measurement period for rotating the carousel at a constant speed,
the length of the container setting period and the length of the fluorescence measurement period are constant, and the container setting period and the fluorescence measurement period are repeated in a predetermined cycle.

2. The nucleic acid analyzer according to claim 1, wherein each of the respective light sources of each of the plurality of detectors is configured to generate excitation light having a wavelength different from one another and each of the plurality of detectors comprise a detection element, and wherein each detection element is configured to detect fluorescence having a wavelength different from another detection element.

3. The nucleic acid analyzer according to claim 1, wherein each of the plurality of detectors is selected such that a difference between wavelengths of excitation lights generated by light sources of the adjacent two detectors is larger than a predetermined wavelength difference, and a difference between wavelengths of fluorescences detected by detection elements of the adjacent two detectors is larger than a predetermined wavelength difference.

4. The nucleic acid analyzer according to claim 1, wherein each of the respective light sources of each of the plurality of detectors is configured to generate excitation light having an identical wavelength and each of the plurality of detectors comprise a detection element configured to detect fluorescence having an identical wavelength.

5. The nucleic acid analyzer according to claim 4, wherein amplification gains with respect to output signals from the plurality of detectors are set to be different from one another.

6. The nucleic acid analyzer according to claim 4, wherein resolutions of output signals from the plurality of detectors are set to be different from one another.

7. The nucleic acid analyzer according to claim 1, wherein a douser is provided between two adjacent detectors of the plurality of detectors.

8. The nucleic acid analyzer according to claim 1, wherein each of the plurality of detectors is provided with an openable and closable shutter; and when the detector optically detects a reaction solution in the reaction container, the shutter opens; and when the detector does not optically detect the reaction solution in the reaction container, the shutter closes.

9. The nucleic acid analyzer according to claim 1, wherein the light source of the detecting device comprises a light-emitting diode, and the detection element comprises a photodiode.

10. The nucleic acid analyzer according to claim 1, comprising a slot for removably supporting each detector, wherein by moving the detector along the slot, the detector can be removed or attached.

11. The nucleic acid analyzer according to claim 1, wherein there is provided a temperature controlling device for keeping temperatures of the reaction container and a reaction liquid in the reaction container at predetermined temperatures.

12. The nucleic acid analyzer according to claim 11, wherein the temperature controlling device comprises a fan, a heat source, and a temperature sensor.

13. The nucleic acid analyzer according to claim 11, wherein the temperature controlling device comprises a heat source and a temperature sensor which are provided in the carousel.

14. The nucleic acid analyzer according to claim 1, wherein there is provided a casing for accommodating at least the carousel and the reaction container; the casing comprises an openable and closable gate; and the reaction container can be taken in and out via the gate.

15. The nucleic acid analyzer according to claim 1, wherein the detectors are arranged at regular intervals along the circumference of the carousel.

16. The nucleic acid analyzer according to claim 1, wherein in the fluorescence measurement period, the detector is configured to measure fluorescence intensity when the reaction container passes a detection position on the detector.

* * * * *